US00PP21823P2

(12) United States Plant Patent

Nouws et al.

(10) Patent No.: US PP21,823 P2
(45) Date of Patent: Mar. 29, 2011

(54) *EUONYMUS* PLANT NAMED 'HAPPINESS'

(50) Latin Name: *Euonymus japonicus*
Varietal Denomination: Happiness

(75) Inventors: Johan Nouws, Zundert (NL); Guus Nouws, Zundert (NL)

(73) Assignee: Van Vliet New Plants BV, Stroe (NL)

( * ) Notice: Subject to any disclaimer, the term of this patent is extended or adjusted under 35 U.S.C. 154(b) by 0 days.

(21) Appl. No.: 12/592,795

(22) Filed: Dec. 3, 2009

(51) Int. Cl.
*A01H 5/00* (2006.01)

(52) U.S. Cl. ..... Plt./246

(58) Field of Classification Search ..... Plt./246
See application file for complete search history.

(56) References Cited

PUBLICATIONS

UPOV-ROM GTITM, Plant Variety Database, 2010/10, GTI Jouve Retrieval Software, Citation for plant 'Happiness'.*

* cited by examiner

*Primary Examiner*—Susan B McCormick Ewoldt
(74) *Attorney, Agent, or Firm*—Jondle & Associates, P.C.

(57) ABSTRACT

A *Euonymus* variety particularly distinguished by a spreading to broad upright growth habit, a flattened globular plant shape with low to moderate vigor, young shoots colored light yellow-green and fading to deep yellow, and dark green mature foliage, is disclosed.

2 Drawing Sheets

Genus and species: *Euonymus japonicus.*

Variety denomination: 'Happiness'.

BACKGROUND OF THE NEW PLANT

The present invention comprises a new and distinct variety of *Euonymus*, botanically known as *Euonymus japonicus*, a variety of the Japanese Spindle shrub, and hereinafter referred to by the variety name 'Happiness'. The new variety originated from a naturally-occuring branch mutation of the *Euonymus japonicus* parent 'Microphyllus Aureovariegatus' (unpatented) in Zundert, The Netherlands in October 2005.

The new variety was first propagated in early summer 2006 in Zundert, The Netherlands, and has been asexually reproduced repeatedly by softwood cuttings in Stroe, The Netherlands for at least four generations (since early summer 2006). The present invention has been found to retain its distinctive characteristics through successive asexual propagations.

'Happiness' has not been made publicly available or sold more than one year prior to filing of this application.

REFERENCE TO PLANT BREEDERS RIGHTS

Community Plant Variety Rights for this variety were granted on Mar. 9, 2009.

SUMMARY OF THE INVENTION

The following are the most outstanding and distinguishing characteristics of the new variety when grown under normal horticultural practices in Stroe, The Netherlands.

1. A spreading to broad upright growth habit;
2. A flattened globular plant shape with low to moderate vigor;

3. Young shoots colored light yellow-green and fading to deep yellow; and
4. Dark green mature foliage.

DESCRIPTION OF THE PHOTOGRAPHS

This new *Euonymus* plant is illustrated by the accompanying photographs which show overall plant habit and foliage of the plant. The colors shown are as true as can be reasonably obtained by conventional photographic procedures. The photos are of a 3-year-old plant grown outdoors in a 17 cm container in Stroe, The Netherlands in September 2009.

DESCRIPTION OF THE NEW VARIETY

Figure 1:
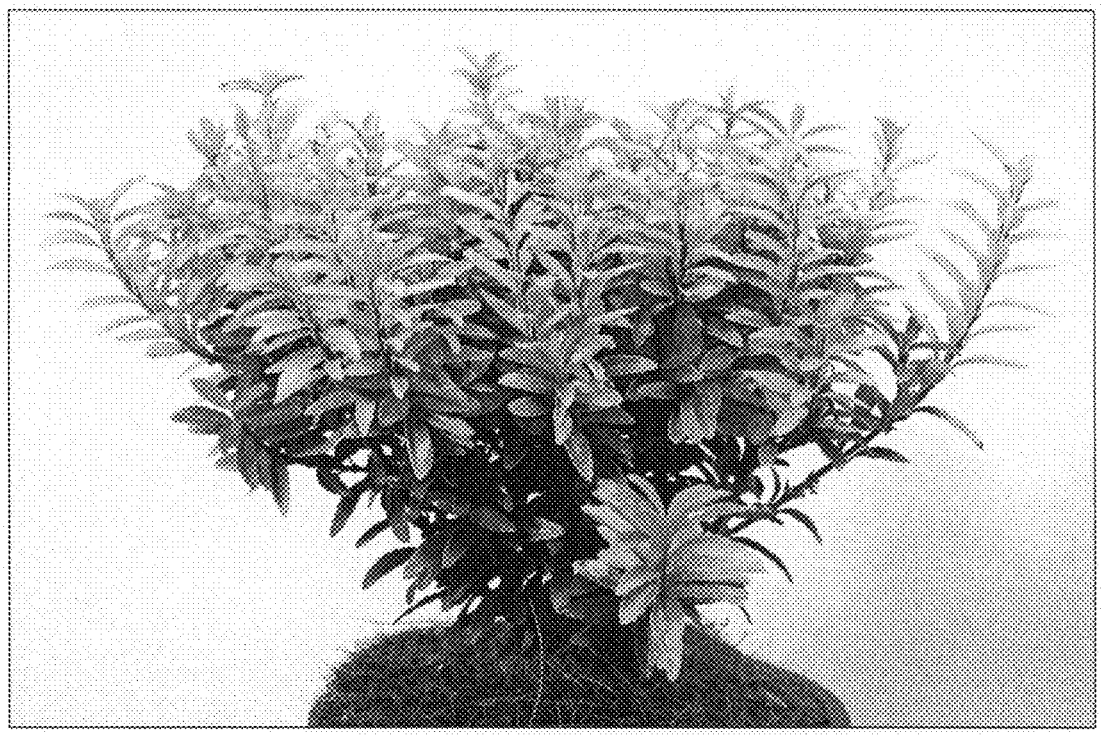
FIG. 1 shows the overall plant habit including foliage.
Figure 2:
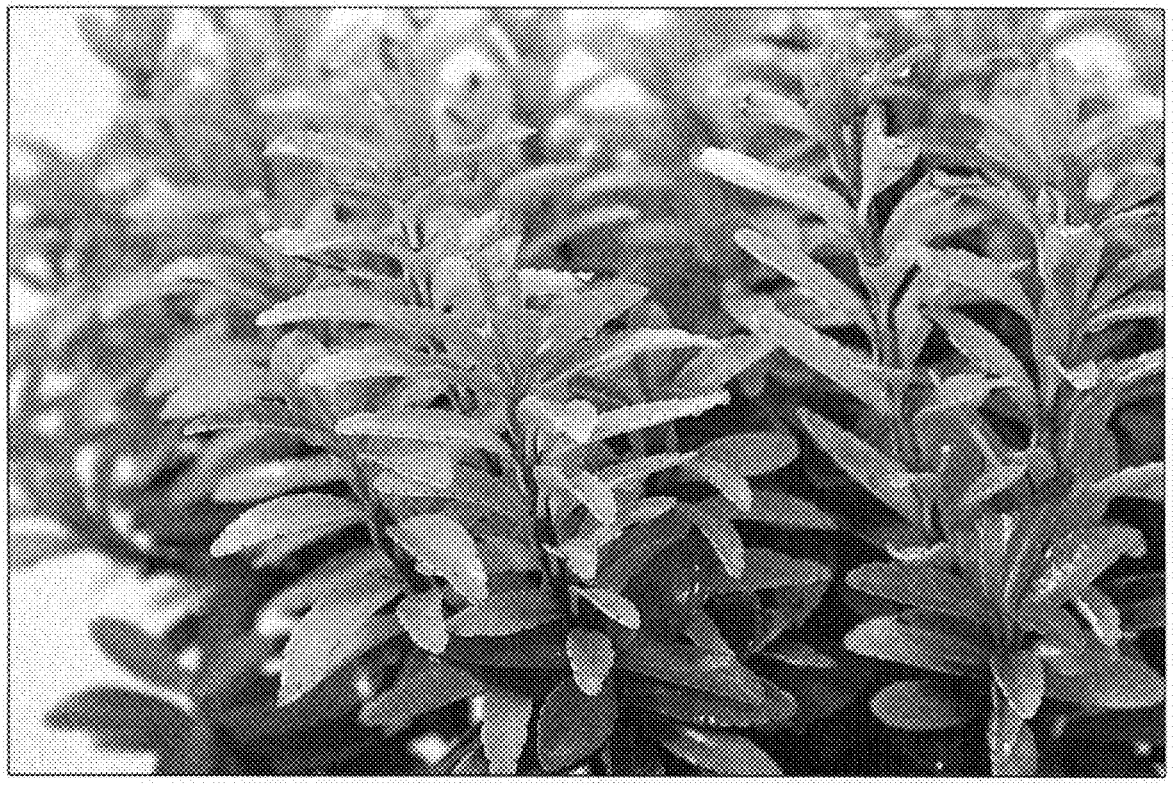
FIG. 2 shows a close-up view of the immature and mature foliage.

The following detailed descriptions set forth the distinctive characteristics of 'Happiness'. The data which define these characteristics were collected from asexual reproductions carried out in Stroe, The Netherlands. The plant history was taken on 3-year-old plants grown in 17 cm containers outdoors, in September 2009. The range of daytime temperature was 14° C. to 32° C. and the range of night-time temperature was from 6° C. to 18° C. No growth retardants were used. The color readings were determined under natural light. Color references are to The R.H.S. Colour Chart of The Royal Horticultural Society of London (R.H.S.) (2007).

DESCRIPTION OF THE NEW PLANT

Classification:

*Family.*—Celastraceae.

*Botanical name.*—*Euonymus japonicas.*

*Common name.*—Japanese Spindle.

*Denomination.*—'Happiness'.

Plant:

*Form and habit.*—Perrenial shrub.

*Growth and branching habit.*—Spreading to broadly upright; pinching will improve branching substantially.

*Plant shape.*—Flattened globular.

*Height.*—19.0 cm.

*Width* (*spread*).—25.6 cm.

*Growth rate and vigor.*—Low to moderate.

*Time to produce a finished plant.*—Approximately 12 months.

*Outdoor plant performance.*—Use in 11.0 cm pots or larger, or in flower beds.

*Fragrance.*—Absent.

*High temperature tolerance.*—Unknown, at least up to 35° C.

*Low temperature tolerance.*—Unknown, hardy to at least USDA Zone 7.

*Roots.*—No root structures.

Branches:

*Branching.*—Basal; free-branching.

*Total number of lateral branches.*—51.

*Length.*—9.3 cm.

*Diameter.*—0.2 cm.

*Internode length.*—0.6 cm.

*Appearance/shape.*—Rounded; slightly glossy.

*Strength.*—Strong.

*Aspect.*—Rounded.

*Color.*—Immature branches are RHS 143A and RHS 143B (Yellow-green); older branches RHS 137A and 137B (Green).

*Pubescence.*—Absent.

Leaves:

*Arrangement.*—Single and opposite.

*Quantity per lateral branch.*—30 (15 pairs).

*Shape.*—Elliptic.

*Apex.*—Obtuse.

*Base.*—Short attenuate.

*Margin.*—Crenate.

*Texture and appearance* (*both surfaces*).—Smooth, very glossy; no pubescence.

*Size.*—Length: 2.0 cm. Width: 0.7 cm.

*Emerging leaf.*—Color: Upper surface: RHS N144C (Yellow-green). Lower surface: RHS N144D (Yellow-green).

*Immature leaf* (1-*year old*).—Color: Upper surface: RHS 9A to 9B (Yellow). Lower surface: RHS 11A (Yellow).

*Mature leaf.*—Color: Upper surface: Between RHS 139A (Green) and RHS 147A (Yellow-green), but darker. Lower surface: RHS 137C to RHS 137D (Green).

*Venation pattern.*—Pinnate.

*Vein color.*—Upper surface: RHS 138A (Green). Lower surface: RHS 147A to 147B (Yellow-green).

*Petioles.*—Length: 0.4 cm. Diameter: 0.1 cm. Color: RHS 144A (Yellow-green).

*Durability of foliage to stresses.*—High.

Inflorescence: No flowers observed to date.

Fruit and seed set: No seed set observed.

Disease and insect resistance: Average/typical of the species; no special observations made.

COMPARISON WITH PARENTAL AND COMMERCIAL VARIETYS

'Happiness' differs from the female parent 'Microphyllus Aureovariegatus' (unpatented) in that 'Happiness' has yellow-green to green foliage, while 'Microphyllus Aureovariegatus' has variegated foliage.

'Happiness' differs from the commercial comparison variety 'Microphyllus' (unpatented) in that 'Happiness' has yellow-green to green foliage, while 'Microphyllus' has green foliage.

We claim:

1. A new and distinct variety of *Euonymus* plant as shown and described herein.

* * * * *